(12) United States Patent
Steward et al.

(10) Patent No.: US 11,559,437 B2
(45) Date of Patent: Jan. 24, 2023

(54) MULTI-LAYERED WOUND DRESSING AND METHOD OF MANUFACTURE

(71) Applicant: Smith & Nephew PLC, Watford (GB)

(72) Inventors: Daniel Lee Steward, Hull (GB); Emma Cole, Hull (GB); Hannah Bailey Sidebottom, Lincoln (GB); Neil Patrick, Hull (GB)

(73) Assignee: Smith & Nephew PLC, Watford (GB)

( * ) Notice: Subject to any disclaimer, the term of this patent is extended or adjusted under 35 U.S.C. 154(b) by 848 days.

(21) Appl. No.: 16/345,196

(22) PCT Filed: Oct. 24, 2017

(86) PCT No.: PCT/EP2017/077154
§ 371 (c)(1),
(2) Date: Apr. 25, 2019

(87) PCT Pub. No.: WO2018/077872
PCT Pub. Date: May 3, 2018

(65) Prior Publication Data
US 2019/0274889 A1    Sep. 12, 2019

(30) Foreign Application Priority Data
Oct. 28, 2016   (GB) ...................................... 1618298

(51) Int. Cl.
*A61F 13/00* (2006.01)
*A61F 13/02* (2006.01)
(Continued)

(52) U.S. Cl.
CPC .. *A61F 13/00029* (2013.01); *A61F 13/00038* (2013.01); *A61F 13/00068* (2013.01); *A61F 13/0226* (2013.01); *A61F 13/0286* (2013.01); *A61M 1/90* (2021.05); *A61F 2013/00097* (2013.01); *A61F 2013/00548* (2013.01);
(Continued)

(58) Field of Classification Search
None
See application file for complete search history.

(56) References Cited

U.S. PATENT DOCUMENTS 730,062 A    6/1903   Widmer
1,052,274 A  2/1913   Purdy
(Continued)

FOREIGN PATENT DOCUMENTS

CN   101002707 A   7/2007
EP   0053936 A2    6/1982
(Continued)

OTHER PUBLICATIONS

Brief Communication—Letter from the Proprietor of the Patent dated Jun. 16, 2020, for the Opposition of European Patent No. EP2731564, 19 pages.
(Continued)

*Primary Examiner* — Kim M Lewis
(74) *Attorney, Agent, or Firm* — Knobbe, Martens, Olson & Bear LLP (57) ABSTRACT

A multi-layered wound dressing including a fibrous absorbent layer for absorbing exudate from a wound site. The wound dressing also includes a support layer configured to reduce shrinkage of at least a portion of the wound dressing.

20 Claims, 5 Drawing Sheets

(51) Int. Cl.
*A61M 1/00* (2006.01)
*A61F 13/15* (2006.01)
(52) U.S. Cl.
CPC .............. *A61F 2013/00608* (2013.01); *A61F 2013/1591* (2013.01)

(56) References Cited

U.S. PATENT DOCUMENTS

| | | |
|---|---|---|
| 2,054,768 A | 9/1936 | Gale, Jr. et al. |
| 2,233,209 A | 2/1941 | Herzog |
| 2,280,506 A | 4/1942 | Betts |
| 2,682,873 A | 7/1954 | Idnis et al. |
| 2,905,174 A | 9/1959 | Smith |
| 2,992,644 A | 7/1961 | Plantinga et al. |
| 3,043,301 A | 7/1962 | Plantinga et al. |
| 3,156,242 A | 11/1964 | Crowe, Jr. et al. |
| 3,204,277 A | 9/1965 | Sierik et al. |
| 3,301,429 A | 1/1967 | McClain |
| 3,416,524 A | 12/1968 | Meier |
| 3,529,597 A | 9/1970 | Fuzak et al. |
| 3,616,154 A | 10/1971 | Dow et al. |
| 3,687,136 A | 8/1972 | Carmody |
| 4,212,296 A | 7/1980 | Schaar |
| 4,649,909 A | 3/1987 | Thompson |
| 4,798,603 A | 1/1989 | Meyer et al. |
| 4,834,735 A | 5/1989 | Alemany et al. |
| 4,846,164 A | 7/1989 | Martz |
| 4,901,714 A | 2/1990 | Jensen |
| 4,968,181 A | 11/1990 | Goldman |
| 4,973,325 A | 11/1990 | Sherrod et al. |
| 4,988,344 A | 1/1991 | Reising et al. |
| 4,988,345 A | 1/1991 | Reising |
| 5,018,515 A | 5/1991 | Gilman |
| 5,021,050 A | 6/1991 | Iskra |
| 5,037,409 A | 8/1991 | Chen et al. |
| 5,065,600 A | 11/1991 | Byles |
| 5,115,801 A | 5/1992 | Cartmell et al. |
| 5,124,197 A | 6/1992 | Bernardin et al. |
| 5,149,334 A | 9/1992 | Lahrman et al. |
| 5,151,091 A | 9/1992 | Glaug et al. |
| 5,160,328 A | 11/1992 | Cartmell et al. |
| 5,171,391 A | 12/1992 | Chmielewski et al. |
| 5,175,046 A | 12/1992 | Nguyen |
| 5,176,663 A | 1/1993 | Svedman et al. |
| 5,197,945 A | 3/1993 | Cole et al. |
| 5,217,445 A | 6/1993 | Young et al. |
| 5,236,427 A | 8/1993 | Hamajima et al. |
| 5,242,435 A | 9/1993 | Murji et al. |
| 5,257,982 A | 11/1993 | Cohen et al. |
| 5,271,987 A | 12/1993 | Iskra |
| 5,281,208 A | 1/1994 | Thompson et al. |
| 5,294,478 A | 3/1994 | Wanek et al. |
| 5,296,290 A | 3/1994 | Brassington |
| 5,314,743 A | 5/1994 | Meirowitz et al. |
| 5,318,554 A | 6/1994 | Young et al. |
| 5,330,456 A | 7/1994 | Robinson |
| 5,336,219 A | 8/1994 | Krantz |
| 5,342,336 A | 8/1994 | Meirowitz et al. |
| 5,348,547 A | 9/1994 | Payne et al. |
| 5,354,261 A | 10/1994 | Clark et al. |
| 5,356,405 A | 10/1994 | Thompson et al. |
| 5,360,420 A | 11/1994 | Cook et al. |
| 5,364,381 A | 11/1994 | Soga et al. |
| 5,364,382 A | 11/1994 | Latimer et al. |
| 5,366,451 A | 11/1994 | Levesque |
| 5,368,909 A | 11/1994 | Langdon et al. |
| 5,368,926 A | 11/1994 | Thompson et al. |
| 5,374,260 A | 12/1994 | Lemay et al. |
| 5,380,294 A | 1/1995 | Persson |
| 5,382,245 A | 1/1995 | Thompson et al. |
| 5,387,208 A | 2/1995 | Ashton et al. |
| 5,387,209 A | 2/1995 | Yamamoto et al. |
| 5,397,316 A | 3/1995 | LaVon et al. |
| 5,401,267 A | 3/1995 | Couture-Dorschner et al. |
| 5,425,725 A | 6/1995 | Tanzer et al. |
| 5,431,643 A | 7/1995 | Ouellette et al. |
| 5,437,651 A | 8/1995 | Todd et al. |
| 5,447,492 A | 9/1995 | Cartmell et al. |
| 5,454,800 A | 10/1995 | Hirt et al. |
| 5,456,660 A | 10/1995 | Reich et al. |
| 5,465,735 A | 11/1995 | Patel |
| 5,470,326 A | 11/1995 | Dabi et al. |
| H1511 H | 12/1995 | Chappell et al. |
| 5,480,377 A | 1/1996 | Cartmell et al. |
| 5,486,167 A | 1/1996 | Dragoo et al. |
| 5,487,736 A | 1/1996 | Van Phan |
| 5,497,788 A | 3/1996 | Inman et al. |
| 5,500,270 A | 3/1996 | Langdon et al. |
| 5,505,719 A | 4/1996 | Cohen et al. |
| 5,509,914 A | 4/1996 | Osborn, III |
| 5,514,120 A | 5/1996 | Johnston et al. |
| 5,520,629 A | 5/1996 | Heinecke et al. |
| 5,525,407 A | 6/1996 | Yang |
| 5,536,264 A | 7/1996 | Hsueh et al. |
| 5,538,500 A | 7/1996 | Peterson |
| H1585 H | 8/1996 | Ahr |
| 5,545,155 A | 8/1996 | Hseih et al. |
| 5,549,584 A | 8/1996 | Gross |
| 5,549,589 A | 8/1996 | Horney et al. |
| 5,562,107 A | 10/1996 | Lavender et al. |
| 5,562,646 A | 10/1996 | Goldman et al. |
| 5,562,650 A | 10/1996 | Everett et al. |
| 5,579,765 A | 12/1996 | Cox et al. |
| 5,591,148 A | 1/1997 | McFall et al. |
| 5,591,149 A | 1/1997 | Cree et al. |
| 5,593,395 A | 1/1997 | Martz |
| 5,603,707 A | 2/1997 | Trombetta et al. |
| 5,603,946 A | 2/1997 | Constantine |
| 5,609,588 A | 3/1997 | DiPalma et al. |
| 5,613,960 A | 3/1997 | Mizutani |
| 5,614,283 A | 3/1997 | Potnis et al. |
| 5,614,295 A | 3/1997 | Quincy, III et al. |
| 5,628,736 A | 5/1997 | Thompson |
| 5,632,731 A | 5/1997 | Patel |
| H1657 H | 6/1997 | Hammons et al. |
| 5,634,915 A | 6/1997 | Osterdahl |
| 5,636,643 A | 6/1997 | Argenta et al. |
| 5,637,080 A | 6/1997 | Geng |
| 5,643,238 A | 7/1997 | Baker |
| 5,645,081 A | 7/1997 | Argenta et al. |
| 5,648,142 A | 7/1997 | Phillips |
| 5,649,915 A | 7/1997 | Chauvette et al. |
| 5,649,916 A | 7/1997 | DiPalma et al. |
| 5,662,599 A | 9/1997 | Reich et al. |
| 5,665,082 A | 9/1997 | Boulanger |
| 5,669,895 A | 9/1997 | Murakami et al. |
| 5,675,079 A | 10/1997 | Gilman et al. |
| 5,683,354 A | 11/1997 | Levy |
| 5,700,254 A | 12/1997 | McDowall et al. |
| 5,702,356 A | 12/1997 | Hathman |
| 5,704,905 A | 1/1998 | Jensen et al. |
| 5,713,384 A | 2/1998 | Roach et al. |
| 5,713,842 A | 2/1998 | Kay |
| 5,716,703 A | 2/1998 | Payne |
| 5,728,084 A | 3/1998 | Palumbo et al. |
| 5,728,085 A | 3/1998 | Widlund et al. |
| 5,733,273 A | 3/1998 | Ahr |
| 5,752,945 A | 5/1998 | Mosley et al. |
| 5,762,641 A | 6/1998 | Bewick-Sonntag et al. |
| 5,788,684 A | 8/1998 | Abuto et al. |
| 5,801,107 A | 9/1998 | Everhart et al. |
| 5,810,798 A | 9/1998 | Finch et al. |
| 5,817,081 A | 10/1998 | LaVon et al. |
| 5,820,578 A | 10/1998 | Johansen |
| 5,827,213 A | 10/1998 | Jensen |
| 5,827,254 A | 10/1998 | Trombetta et al. |
| 5,830,202 A | 11/1998 | Bogdanski et al. |
| 5,837,627 A | 11/1998 | Halabisky et al. |
| 5,840,052 A | 11/1998 | Johns |
| 5,843,025 A | 12/1998 | Shaari |
| 5,843,064 A | 12/1998 | Koczab |
| 5,855,572 A | 1/1999 | Schmidt |
| 5,865,822 A | 2/1999 | Hamajima et al. |
| 5,865,824 A | 2/1999 | Chen et al. |

(56) References Cited

U.S. PATENT DOCUMENTS

| | | |
|---|---|---|
| 5,873,867 A | 2/1999 | Coles et al. |
| 5,877,097 A | 3/1999 | West et al. |
| 5,891,120 A | 4/1999 | Chmielewski |
| 5,895,379 A | 4/1999 | Litchholt et al. |
| 5,897,541 A | 4/1999 | Uitenbroek et al. |
| 5,916,507 A | 6/1999 | Dabi et al. |
| 5,925,026 A | 7/1999 | Arteman et al. |
| 5,931,823 A | 8/1999 | Stokes et al. |
| 5,938,995 A | 8/1999 | Koltisko, Jr. et al. |
| 5,941,863 A | 8/1999 | Guidotti et al. |
| 5,947,945 A | 9/1999 | Cree et al. |
| 5,951,535 A | 9/1999 | Fujiwara et al. |
| 5,961,506 A | 10/1999 | Guidotti et al. |
| 5,968,027 A | 10/1999 | Cole et al. |
| 5,989,478 A | 11/1999 | Ouellette et al. |
| 6,022,610 A | 2/2000 | Phan et al. |
| 6,037,518 A | 3/2000 | Guidotti et al. |
| 6,040,493 A | 3/2000 | Cooke et al. |
| 6,060,638 A | 5/2000 | Paul et al. |
| 6,068,620 A | 5/2000 | Chmielewski |
| 6,071,267 A | 6/2000 | Zamierowski |
| 6,075,177 A | 6/2000 | Bahia et al. |
| 6,077,526 A | 6/2000 | Scully et al. |
| 6,096,015 A | 8/2000 | Yeo et al. |
| 6,103,953 A | 8/2000 | Cree et al. |
| 6,103,954 A | 8/2000 | Grondin et al. |
| 6,107,539 A | 8/2000 | Palumbo et al. |
| 6,124,520 A | 9/2000 | Roberts |
| 6,124,521 A | 9/2000 | Roberts |
| 6,127,595 A | 10/2000 | Makoui et al. |
| 6,142,982 A | 11/2000 | Hunt et al. |
| 6,168,849 B1 | 1/2001 | Braverman et al. |
| 6,191,340 B1 | 2/2001 | Carlucci et al. |
| 6,206,865 B1 | 3/2001 | Chen et al. |
| 6,223,383 B1 | 5/2001 | Vanputten |
| 6,235,966 B1 | 5/2001 | Magnusson et al. |
| 6,264,776 B1 | 7/2001 | DiPalma |
| 6,294,710 B1 | 9/2001 | Schmidt et al. |
| 6,297,423 B1 | 10/2001 | Schoenfeldt et al. |
| 6,344,036 B1 | 2/2002 | Ivansson |
| 6,345,623 B1 | 2/2002 | Heaton et al. |
| 6,362,390 B1 | 3/2002 | Carlucci et al. |
| 6,369,292 B1 | 4/2002 | Strack et al. |
| 6,372,952 B1 | 4/2002 | Lash et al. |
| 6,403,857 B1 | 6/2002 | Gross et al. |
| 6,468,295 B2 | 10/2002 | Augustine et al. |
| 6,497,689 B1 | 12/2002 | Schmidt et al. |
| 6,506,175 B1 | 1/2003 | Goldstein |
| 6,506,960 B1 | 1/2003 | Young et al. |
| 6,521,813 B1 | 2/2003 | Chihani |
| 6,528,696 B1 | 3/2003 | Ireland |
| 6,534,149 B1 | 3/2003 | Daley et al. |
| 6,545,194 B1 | 4/2003 | Schmidt et al. |
| 6,551,295 B1 | 4/2003 | Schmidt et al. |
| 6,570,057 B1 | 5/2003 | Schmidt et al. |
| 6,570,058 B1 | 5/2003 | Fuchs et al. |
| 6,573,424 B1 | 6/2003 | Raidel et al. |
| 6,586,653 B2 | 7/2003 | Graeme, III et al. |
| 6,610,898 B1 | 8/2003 | Magnusson et al. |
| 6,610,903 B1 | 8/2003 | Latimer et al. |
| 6,613,028 B1 | 9/2003 | Daley et al. |
| 6,613,953 B1 | 9/2003 | Altura |
| 6,613,955 B1 | 9/2003 | Lindsay et al. |
| 6,626,891 B2 | 9/2003 | Ohmstede |
| 6,630,611 B1 | 10/2003 | Malowaniec |
| 6,648,862 B2 | 11/2003 | Watson |
| 6,664,439 B1 | 12/2003 | Arndt et al. |
| 6,683,229 B1 | 1/2004 | Ehrnsperger et al. |
| 6,685,681 B2 | 2/2004 | Lockwood et al. |
| 6,706,940 B2 | 3/2004 | Worthley |
| 6,719,742 B1 | 4/2004 | McCormack et al. |
| 6,727,403 B1 | 4/2004 | Ehrnsperger et al. |
| 6,752,794 B2 | 6/2004 | Lockwood et al. |
| 6,762,337 B2 | 7/2004 | Boukanov et al. |
| 6,764,459 B1 | 7/2004 | Donaldson |
| 6,776,769 B2 | 8/2004 | Smith |
| 6,783,837 B1 | 8/2004 | Creagan et al. |
| 6,787,682 B2 | 9/2004 | Gilman |
| 6,835,192 B1 | 12/2004 | Guidotti et al. |
| 6,838,589 B2 | 1/2005 | Liedtke et al. |
| 6,841,715 B2 | 1/2005 | Roberts |
| 6,878,647 B1 * | 4/2005 | Rezai .................... B32B 37/144 442/18 |
| 6,936,037 B2 | 8/2005 | Bubb et al. |
| 6,951,553 B2 | 10/2005 | Bubb et al. |
| 6,960,181 B2 | 11/2005 | Stevens |
| 6,998,511 B2 | 2/2006 | Worthley |
| 7,004,915 B2 | 2/2006 | Boynton et al. |
| 7,049,478 B1 | 5/2006 | Smith |
| 7,108,683 B2 | 9/2006 | Zamierowski |
| 7,112,712 B1 | 9/2006 | Ancell |
| 7,118,545 B2 | 10/2006 | Boyde |
| 7,122,023 B1 | 10/2006 | Hinoki |
| 7,122,712 B2 | 10/2006 | Lutri et al. |
| 7,183,345 B2 | 2/2007 | Kim |
| 7,195,624 B2 | 3/2007 | Lockwood et al. |
| 7,294,751 B2 | 11/2007 | Propp et al. |
| 7,294,752 B1 | 11/2007 | Propp |
| 7,381,859 B2 | 6/2008 | Hunt et al. |
| 7,429,689 B2 | 9/2008 | Chen et al. |
| 7,438,705 B2 | 10/2008 | Karpowicz et al. |
| 7,476,205 B2 | 1/2009 | Erdmann |
| 7,507,870 B2 | 3/2009 | Nielsen et al. |
| 7,511,187 B2 | 3/2009 | Kelly |
| 7,563,940 B2 | 7/2009 | Kurata |
| 7,569,742 B2 | 8/2009 | Haggstrom et al. |
| 7,576,256 B2 | 8/2009 | Bjornberg et al. |
| 7,605,298 B2 | 10/2009 | Bechert et al. |
| 7,615,036 B2 | 11/2009 | Joshi et al. |
| 7,622,629 B2 | 11/2009 | Aali |
| 7,645,269 B2 | 1/2010 | Zamierowski |
| 7,676,257 B2 | 3/2010 | Suryanarayanan et al. |
| 7,708,724 B2 | 5/2010 | Weston |
| 7,722,582 B2 | 5/2010 | Lina et al. |
| 7,723,561 B2 | 5/2010 | Propp |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,794,438 B2 | 9/2010 | Henley et al. |
| 7,838,719 B2 | 11/2010 | Hilton, Jr. |
| 7,838,723 B2 | 11/2010 | Schmidt et al. |
| 7,909,805 B2 | 3/2011 | Weston |
| 7,922,703 B2 | 4/2011 | Riesinger |
| 7,935,066 B2 | 5/2011 | Shives et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,988,673 B2 | 8/2011 | Wright et al. |
| 8,021,347 B2 | 9/2011 | Vitaris et al. |
| 8,062,272 B2 | 11/2011 | Weston |
| 8,092,436 B2 | 1/2012 | Christensen |
| 8,147,468 B2 | 4/2012 | Barta et al. |
| 8,152,785 B2 | 4/2012 | Vitaris |
| 8,162,907 B2 | 4/2012 | Heagle |
| 8,168,848 B2 | 5/2012 | Lockwood et al. |
| 8,188,331 B2 | 5/2012 | Barta et al. |
| 8,202,261 B2 | 6/2012 | Kazala, Jr. et al. |
| 8,212,101 B2 | 7/2012 | Propp |
| 8,241,261 B2 | 8/2012 | Randolph et al. |
| 8,246,606 B2 | 8/2012 | Stevenson et al. |
| 8,252,971 B2 | 8/2012 | Aali et al. |
| 8,314,283 B2 | 11/2012 | Kingsford et al. |
| 8,328,858 B2 | 12/2012 | Barsky et al. |
| 8,372,050 B2 | 2/2013 | Jaeb et al. |
| 8,376,972 B2 | 2/2013 | Fleischmann |
| 8,382,731 B2 | 2/2013 | Johannison |
| 8,403,899 B2 | 3/2013 | Sherman |
| 8,404,921 B2 | 3/2013 | Lee et al. |
| 8,425,478 B2 | 4/2013 | Olson |
| 8,444,611 B2 | 5/2013 | Wilkes et al. |
| 8,449,508 B2 | 5/2013 | Coulthard et al. |

(56) References Cited

U.S. PATENT DOCUMENTS

| | | |
|---|---|---|
| 8,481,804 B2 * | 7/2013 | Timothy ............ A61F 13/00021 602/53 |
| 8,513,481 B2 | 8/2013 | Gergely et al. |
| 8,535,296 B2 | 9/2013 | Blott et al. |
| 8,545,466 B2 | 10/2013 | Andresen et al. |
| 8,663,198 B2 | 3/2014 | Buan et al. |
| 8,680,360 B2 | 3/2014 | Greener et al. |
| 8,708,998 B2 | 4/2014 | Weston et al. |
| 8,715,256 B2 | 5/2014 | Greener |
| 8,722,961 B2 | 5/2014 | Vinton et al. |
| 8,764,732 B2 | 7/2014 | Hartwell |
| 8,791,316 B2 | 7/2014 | Greener |
| 8,795,247 B2 | 8/2014 | Bennett et al. |
| 8,801,685 B2 | 8/2014 | Armstrong et al. |
| 8,814,842 B2 | 8/2014 | Coulthard et al. |
| 8,843,327 B2 | 9/2014 | Vernon-Harcourt et al. |
| 8,916,742 B2 | 12/2014 | Smith |
| 8,986,270 B2 | 3/2015 | Johannison et al. |
| 9,033,942 B2 | 5/2015 | Vess |
| 9,061,095 B2 | 6/2015 | Adie et al. |
| 9,220,822 B2 | 12/2015 | Hartwell |
| 9,254,353 B2 | 2/2016 | Locke et al. |
| 9,265,665 B2 | 2/2016 | Robinson et al. |
| 9,579,411 B2 | 2/2017 | Addison et al. |
| 2001/0000795 A1 | 5/2001 | Bolian, II et al. |
| 2001/0016985 A1 | 8/2001 | Insley et al. |
| 2001/0018308 A1 | 8/2001 | Quick et al. |
| 2001/0027302 A1 | 10/2001 | Glaug et al. |
| 2001/0027305 A1 | 10/2001 | Raidel et al. |
| 2001/0044610 A1 | 11/2001 | Kim et al. |
| 2001/0051178 A1 | 12/2001 | Blatchford et al. |
| 2001/0053904 A1 | 12/2001 | Abuto |
| 2002/0007167 A1 | 1/2002 | Dan et al. |
| 2002/0007169 A1 | 1/2002 | Graef et al. |
| 2002/0019602 A1 | 2/2002 | Geng |
| 2002/0019614 A1 | 2/2002 | Woon et al. |
| 2002/0026166 A1 | 2/2002 | Graef et al. |
| 2002/0034914 A1 | 3/2002 | De Leon et al. |
| 2002/0035354 A1 | 3/2002 | Mirle et al. |
| 2002/0062113 A1 | 5/2002 | Thomas et al. |
| 2002/0064639 A1 | 5/2002 | Rearick et al. |
| 2002/0087136 A1 | 7/2002 | Widlund |
| 2002/0090511 A1 | 7/2002 | Smith et al. |
| 2002/0110672 A1 | 8/2002 | Muratore-Pallatino et al. |
| 2002/0123728 A1 | 9/2002 | Graef et al. |
| 2002/0133132 A1 | 9/2002 | Copat et al. |
| 2002/0150678 A1 | 10/2002 | Cramer et al. |
| 2002/0165509 A1 | 11/2002 | Baer et al. |
| 2002/0176964 A1 | 11/2002 | Koslow |
| 2002/0177831 A1 | 11/2002 | Daley et al. |
| 2002/0180092 A1 | 12/2002 | Abba et al. |
| 2002/0183704 A1 | 12/2002 | Fields et al. |
| 2003/0009122 A1 | 1/2003 | Veras |
| 2003/0045707 A1 | 3/2003 | West et al. |
| 2003/0045825 A1 | 3/2003 | Etheredge, III |
| 2003/0050617 A1 | 3/2003 | Chen et al. |
| 2003/0069563 A1 | 4/2003 | Johnson |
| 2003/0070780 A1 | 4/2003 | Chen et al. |
| 2003/0073967 A1 | 4/2003 | Wahlstrom et al. |
| 2003/0088229 A1 | 5/2003 | Baker et al. |
| 2003/0088231 A1 | 5/2003 | Yoshimasa et al. |
| 2003/0093044 A1 | 5/2003 | Wahlstrom et al. |
| 2003/0097101 A1 | 5/2003 | Schmidt et al. |
| 2003/0097105 A1 | 5/2003 | Chen et al. |
| 2003/0097113 A1 | 5/2003 | Molee |
| 2003/0105442 A1 | 6/2003 | Johnston et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0124311 A1 | 7/2003 | Cree et al. |
| 2003/0134559 A1 | 7/2003 | Delzer et al. |
| 2003/0135174 A1 | 7/2003 | Benecke et al. |
| 2003/0135177 A1 | 7/2003 | Baker |
| 2003/0150551 A1 | 8/2003 | Baker |
| 2003/0157857 A1 | 8/2003 | Cook et al. |
| 2003/0171729 A1 | 9/2003 | Kaun et al. |
| 2003/0180341 A1 | 9/2003 | Gooch et al. |
| 2003/0190854 A1 * | 10/2003 | Stagray ............... B32B 37/1284 442/381 |
| 2003/0199800 A1 | 10/2003 | Levin |
| 2003/0208175 A1 | 11/2003 | Gross et al. |
| 2003/0212359 A1 | 11/2003 | Butler |
| 2003/0225383 A1 | 12/2003 | Glaug et al. |
| 2004/0019338 A1 | 1/2004 | Litvay et al. |
| 2004/0019339 A1 | 1/2004 | Ranganathan et al. |
| 2004/0019340 A1 | 1/2004 | McBride |
| 2004/0019342 A1 | 1/2004 | Nagasuna et al. |
| 2004/0024102 A1 * | 2/2004 | Hayes ...................... B32B 7/12 524/425 |
| 2004/0024375 A1 | 2/2004 | Litvay |
| 2004/0033750 A1 | 2/2004 | Everett et al. |
| 2004/0049146 A1 | 3/2004 | Kolte et al. |
| 2004/0054343 A1 | 3/2004 | Barnett et al. |
| 2004/0054344 A1 | 3/2004 | Roettger et al. |
| 2004/0065420 A1 | 4/2004 | Graef et al. |
| 2004/0076662 A1 | 4/2004 | Riesinger |
| 2004/0078016 A1 | 4/2004 | Baker |
| 2004/0087927 A1 | 5/2004 | Suzuki |
| 2004/0111074 A1 | 6/2004 | Eliasson |
| 2004/0138602 A1 | 7/2004 | Rossen |
| 2004/0177935 A1 | 9/2004 | Hamed et al. |
| 2004/0181199 A1 | 9/2004 | Moberg-Alehammar et al. |
| 2004/0204696 A1 | 10/2004 | Chen |
| 2004/0230173 A1 | 11/2004 | Barge et al. |
| 2004/0230184 A1 | 11/2004 | Babusik et al. |
| 2004/0241214 A1 | 12/2004 | Kirkwood et al. |
| 2004/0243042 A1 | 12/2004 | Lipman |
| 2004/0243080 A1 | 12/2004 | Baer |
| 2004/0243081 A1 | 12/2004 | Suzuki et al. |
| 2004/0253894 A1 | 12/2004 | Fell et al. |
| 2004/0254552 A1 | 12/2004 | Mangold |
| 2005/0008825 A1 | 1/2005 | Casey et al. |
| 2005/0013992 A1 | 1/2005 | Azad et al. |
| 2005/0015036 A1 | 1/2005 | Lutri et al. |
| 2005/0049566 A1 | 3/2005 | Vukos et al. |
| 2005/0079361 A1 | 4/2005 | Hamed et al. |
| 2005/0096616 A1 | 5/2005 | Arora et al. |
| 2005/0112979 A1 | 5/2005 | Sawyer et al. |
| 2005/0119631 A1 | 6/2005 | Giloh et al. |
| 2005/0136773 A1 | 6/2005 | Yahiaoui et al. |
| 2005/0165371 A1 | 7/2005 | Giacometti |
| 2005/0215965 A1 | 9/2005 | Schmidt et al. |
| 2005/0215967 A1 | 9/2005 | Toro et al. |
| 2005/0222547 A1 | 10/2005 | Beruda et al. |
| 2005/0228353 A1 | 10/2005 | Thomas |
| 2005/0261649 A1 | 11/2005 | Cohen |
| 2005/0267429 A1 | 12/2005 | Cohen |
| 2006/0003604 A1 | 1/2006 | Angerpointner |
| 2006/0009744 A1 | 1/2006 | Erdman et al. |
| 2006/0020250 A1 | 1/2006 | Chester et al. |
| 2006/0058750 A1 | 3/2006 | Di Girolamo et al. |
| 2006/0069366 A1 | 3/2006 | Cole |
| 2006/0069367 A1 | 3/2006 | Waksmundzki et al. |
| 2006/0069375 A1 | 3/2006 | Waksmundzki et al. |
| 2006/0122548 A1 | 6/2006 | Abrams |
| 2006/0122572 A1 | 6/2006 | Suarez |
| 2006/0153904 A1 | 7/2006 | Smith et al. |
| 2006/0161122 A1 | 7/2006 | Erdman et al. |
| 2006/0178650 A1 | 8/2006 | Hakansson et al. |
| 2006/0184147 A1 | 8/2006 | Hamed |
| 2006/0206047 A1 | 9/2006 | Lampe et al. |
| 2006/0206073 A1 | 9/2006 | Crane et al. |
| 2006/0206074 A1 | 9/2006 | Bernal et al. |
| 2006/0241542 A1 | 10/2006 | Gudnason et al. |
| 2006/0282028 A1 | 12/2006 | Howard et al. |
| 2007/0003604 A1 | 1/2007 | Jones |
| 2007/0021697 A1 | 1/2007 | Ginther et al. |
| 2007/0073254 A1 | 3/2007 | Ponomarenko et al. |
| 2007/0078467 A1 | 4/2007 | Mullen |
| 2007/0100308 A1 | 5/2007 | Miyairi |
| 2007/0142804 A1 | 6/2007 | Bernard |
| 2007/0167096 A1 | 7/2007 | Scott |

(56) References Cited

U.S. PATENT DOCUMENTS

| | | |
|---|---|---|
| 2007/0167884 A1 | 7/2007 | Mangrum et al. |
| 2007/0224903 A1 | 9/2007 | Chakravarty et al. |
| 2007/0225663 A1 | 9/2007 | Watt et al. |
| 2007/0254550 A1 | 11/2007 | Hamed et al. |
| 2007/0270070 A1 | 11/2007 | Hamed |
| 2007/0282236 A1 | 12/2007 | LaGreca |
| 2008/0004581 A1 | 1/2008 | Babusik et al. |
| 2008/0015532 A1 | 1/2008 | Waksmundzki |
| 2008/0058691 A1 | 3/2008 | Sorensen |
| 2008/0082075 A1 | 4/2008 | Morrell-Schwartz |
| 2008/0090050 A1 | 4/2008 | Seyler et al. |
| 2008/0091152 A1 | 4/2008 | Asherman |
| 2008/0114317 A1 | 5/2008 | Seyler |
| 2008/0119586 A1 | 5/2008 | Byerly et al. |
| 2008/0147024 A1 | 6/2008 | Potts et al. |
| 2008/0167592 A1 | 7/2008 | Greer |
| 2008/0243100 A1 | 10/2008 | Wu et al. |
| 2008/0254103 A1 | 10/2008 | Harris et al. |
| 2008/0255533 A1 | 10/2008 | Wu et al. |
| 2008/0275409 A1 | 11/2008 | Kane et al. |
| 2008/0312621 A1 | 12/2008 | Hundorf et al. |
| 2008/0312622 A1 | 12/2008 | Hundorf et al. |
| 2009/0062760 A1 | 3/2009 | Wright et al. |
| 2009/0065014 A1 | 3/2009 | Nagata |
| 2009/0076472 A1 | 3/2009 | Goldwasser et al. |
| 2009/0112175 A1 | 4/2009 | Bissah et al. |
| 2009/0204087 A1 | 8/2009 | Herfert et al. |
| 2009/0216168 A1 | 8/2009 | Eckstein |
| 2009/0227935 A1 | 9/2009 | Zanella et al. |
| 2009/0227969 A1 | 9/2009 | Jaeb et al. |
| 2009/0240218 A1 | 9/2009 | Braga et al. |
| 2009/0281471 A1 | 11/2009 | Iwahashi et al. |
| 2009/0293887 A1 | 12/2009 | Wilkes et al. |
| 2009/0299251 A1 | 12/2009 | Buan |
| 2009/0299255 A1 | 12/2009 | Kazala, Jr. et al. |
| 2009/0299340 A1 | 12/2009 | Kazala, Jr. et al. |
| 2010/0010461 A1 | 1/2010 | Herfert et al. |
| 2010/0030171 A1 | 2/2010 | Canada et al. |
| 2010/0036334 A1 | 2/2010 | Heagle et al. |
| 2010/0036342 A1 | 2/2010 | Carlucci et al. |
| 2010/0048072 A1 | 2/2010 | Kauschke et al. |
| 2010/0055158 A1 | 3/2010 | Vitaris et al. |
| 2010/0069858 A1 | 3/2010 | Olson |
| 2010/0084074 A1 | 4/2010 | McClernon et al. |
| 2010/0087767 A1 | 4/2010 | McNeil |
| 2010/0106120 A1 | 4/2010 | Holm |
| 2010/0106121 A1 | 4/2010 | Holm |
| 2010/0121286 A1 | 5/2010 | Locke et al. |
| 2010/0121298 A1 | 5/2010 | Seyler et al. |
| 2010/0122417 A1 | 5/2010 | Vrzalik et al. |
| 2010/0125234 A1 | 5/2010 | Smith |
| 2010/0125258 A1 | 5/2010 | Coulthard et al. |
| 2010/0168695 A1 | 7/2010 | Robles et al. |
| 2010/0179463 A1 | 7/2010 | Greener et al. |
| 2010/0217177 A1 | 8/2010 | Cali et al. |
| 2010/0256545 A1 | 10/2010 | Aali et al. |
| 2010/0256584 A1 | 10/2010 | Litvay |
| 2010/0256586 A1 | 10/2010 | Bergstrom et al. |
| 2010/0262091 A1 | 10/2010 | Larsson |
| 2010/0305526 A1 | 12/2010 | Robinson et al. |
| 2010/0318047 A1 | 12/2010 | Ducker et al. |
| 2010/0318052 A1 | 12/2010 | Ha et al. |
| 2010/0324516 A1 | 12/2010 | Braga et al. |
| 2011/0004172 A1 | 1/2011 | Eckstein et al. |
| 2011/0052664 A1 | 3/2011 | Tennican et al. |
| 2011/0054422 A1 | 3/2011 | Locke et al. |
| 2011/0059329 A1 | 3/2011 | Dobrawa et al. |
| 2011/0060303 A1 | 3/2011 | Bissah et al. |
| 2011/0092927 A1 | 4/2011 | Wilkes et al. |
| 2011/0098621 A1 | 4/2011 | Fabo et al. |
| 2011/0106030 A1 | 5/2011 | Scholz |
| 2011/0112492 A1 | 5/2011 | Bharti et al. |
| 2011/0125119 A1 | 5/2011 | Weismantel et al. |
| 2011/0137222 A1 | 6/2011 | Masini |
| 2011/0152813 A1 | 6/2011 | Ellingson |
| 2011/0178375 A1 | 7/2011 | Forster |
| 2011/0183109 A1 | 7/2011 | Seyler et al. |
| 2011/0184364 A1 | 7/2011 | Biggs et al. |
| 2011/0184370 A1 | 7/2011 | Seyler et al. |
| 2011/0208145 A1 | 8/2011 | Zhang et al. |
| 2011/0213286 A1 | 9/2011 | Riesinger |
| 2011/0218509 A1 | 9/2011 | Dontas |
| 2011/0223413 A1 | 9/2011 | Herfert et al. |
| 2011/0224631 A1 | 9/2011 | Simmons et al. |
| 2011/0238026 A1 | 9/2011 | Zhang et al. |
| 2011/0245788 A1 | 10/2011 | Marquez Canada |
| 2011/0247636 A1 | 10/2011 | Pollack |
| 2011/0257572 A1 | 10/2011 | Locke et al. |
| 2011/0268932 A1 | 11/2011 | Catalan et al. |
| 2012/0004632 A1 | 1/2012 | Zhang et al. |
| 2012/0045639 A1 | 2/2012 | Whitmore et al. |
| 2012/0053547 A1 | 3/2012 | Schroeder et al. |
| 2012/0071848 A1 | 3/2012 | Zhang et al. |
| 2012/0095426 A1 | 4/2012 | Visscher et al. |
| 2012/0101465 A1 | 4/2012 | McGuire, Jr. |
| 2012/0123311 A1 | 5/2012 | Weidemann-Hendrickson et al. |
| 2012/0130332 A1 | 5/2012 | Cotton et al. |
| 2012/0136329 A1 | 5/2012 | Carney |
| 2012/0143158 A1 | 6/2012 | Yang et al. |
| 2012/0172778 A1 | 7/2012 | Rastegar et al. |
| 2012/0197229 A1 | 8/2012 | Buan et al. |
| 2012/0203145 A1 | 8/2012 | Nilsson |
| 2012/0220968 A1 | 8/2012 | Confalone et al. |
| 2012/0232502 A1 | 9/2012 | Lowing |
| 2012/0238932 A1 | 9/2012 | Atteia et al. |
| 2012/0283529 A1 | 11/2012 | Marchand et al. |
| 2012/0302440 A1 | 11/2012 | Theliander et al. |
| 2012/0308780 A1 | 12/2012 | Rottger et al. |
| 2012/0310186 A1 | 12/2012 | Moghe et al. |
| 2012/0310197 A1 | 12/2012 | Thomas |
| 2012/0330252 A1 | 12/2012 | Stokes et al. |
| 2012/0330253 A1 | 12/2012 | Robinson et al. |
| 2013/0012902 A1 | 1/2013 | Rovaniemi |
| 2013/0197460 A1* | 8/2013 | Shaw .................... A61F 13/539 604/368 |
| 2014/0114268 A1 | 4/2014 | Auguste et al. |
| 2015/0159066 A1 | 6/2015 | Hartwell et al. |
| 2015/0174304 A1 | 6/2015 | Askem et al. |
| 2018/0125720 A1 | 5/2018 | Pigg |
| 2019/0110932 A1 | 4/2019 | Mumby et al. |
| 2019/0216651 A1 | 7/2019 | Vitaris et al. |

FOREIGN PATENT DOCUMENTS

| | | |
|---|---|---|
| EP | 0147119 A2 | 7/1985 |
| EP | 0541251 A1 | 5/1993 |
| EP | 0619105 A1 | 10/1994 |
| EP | 0748894 A2 | 12/1996 |
| EP | 0875224 A1 | 11/1998 |
| EP | 0941726 A1 | 9/1999 |
| EP | 1013290 A1 | 6/2000 |
| EP | 1048278 A2 | 11/2000 |
| EP | 1066809 A2 | 1/2001 |
| EP | 1312328 A2 | 5/2003 |
| EP | 1452156 A1 | 9/2004 |
| EP | 1 314 410 | 2/2010 |
| EP | 2161011 A1 | 3/2010 |
| EP | 2366721 A1 | 9/2011 |
| EP | 2659915 B1 | 10/2015 |
| GB | 2272917 A | 6/1994 |
| GB | 2355228 A | 4/2001 |
| GB | 2435422 A | 8/2007 |
| GB | 2435423 A | 8/2007 |
| GB | 2489947 A | 10/2012 |
| GB | 2525494 | 10/2015 |
| JP | 2001145655 A | 5/2001 |
| JP | 2007275185 A | 10/2007 |
| JP | 2008119497 A | 5/2008 |
| WO | WO-9111161 A1 | 8/1991 |
| WO | WO-9111162 A1 | 8/1991 |
| WO | WO-9301778 A1 | 2/1993 |
| WO | WO-9301781 A1 | 2/1993 |
| WO | WO-9311726 A1 | 6/1993 |
| WO | WO-9513042 A1 | 5/1995 |

(56) References Cited

FOREIGN PATENT DOCUMENTS

| | | |
|---|---|---|
| WO | WO-9513779 A1 | 5/1995 |
| WO | WO-9514451 A1 | 6/1995 |
| WO | WO-9516424 A1 | 6/1995 |
| WO | WO-9607783 A1 | 3/1996 |
| WO | WO-9621410 A1 | 7/1996 |
| WO | WO-9711658 A1 | 4/1997 |
| WO | WO-9714384 A1 | 4/1997 |
| WO | WO-9820916 A1 | 5/1998 |
| WO | WO-9822279 A1 | 5/1998 |
| WO | WO-9904830 A1 | 2/1999 |
| WO | WO-9939671 A1 | 8/1999 |
| WO | WO-9945876 A1 | 9/1999 |
| WO | WO-9945878 A1 | 9/1999 |
| WO | WO-9956687 A1 | 11/1999 |
| WO | WO-0000016 A1 | 1/2000 |
| WO | WO-0000127 A1 | 1/2000 |
| WO | WO-0000129 A1 | 1/2000 |
| WO | WO-0000130 A1 | 1/2000 |
| WO | WO-0000131 A1 | 1/2000 |
| WO | WO-0040190 A1 | 7/2000 |
| WO | WO-0042957 A1 | 7/2000 |
| WO | WO-0059438 A1 | 10/2000 |
| WO | WO-0172251 A1 | 10/2001 |
| WO | WO-0190465 A2 | 11/2001 |
| WO | WO-0217840 A1 | 3/2002 |
| WO | WO-0224132 A2 | 3/2002 |
| WO | WO-0226180 A1 | 4/2002 |
| WO | WO-0238096 A2 | 5/2002 |
| WO | WO-02076379 A2 | 10/2002 |
| WO | WO-03057307 A1 | 7/2003 |
| WO | WO-03073971 A2 | 9/2003 |
| WO | WO-2004043321 A1 | 5/2004 |
| WO | WO-2004073566 A1 | 9/2004 |
| WO | WO-2004098474 A1 | 11/2004 |
| WO | WO-2006105305 A1 | 10/2006 |
| WO | WO-2007035038 A1 | 3/2007 |
| WO | WO-2007040606 A2 | 4/2007 |
| WO | WO-2007077214 A1 | 7/2007 |
| WO | WO-2007077216 A1 | 7/2007 |
| WO | WO-2007082538 A1 | 7/2007 |
| WO | WO-2007116347 A2 | 10/2007 |
| WO | WO-2007134516 A1 | 11/2007 |
| WO | WO-2008049277 A1 | 5/2008 |
| WO | WO-2008131895 A1 | 11/2008 |
| WO | WO-2009019227 A2 | 2/2009 |
| WO | WO-2009019229 A2 | 2/2009 |
| WO | WO-2009103031 A1 | 8/2009 |
| WO | WO-2009152021 A2 | 12/2009 |
| WO | WO-2010032951 A2 | 3/2010 |
| WO | WO-2010072395 A1 | 7/2010 |
| WO | WO-2010082872 A1 | 7/2010 |
| WO | WO-2010089448 A1 | 8/2010 |
| WO | WO-2010139926 A1 | 12/2010 |
| WO | WO-2011019476 A1 | 2/2011 |
| WO | WO-2011023275 A1 | 3/2011 |
| WO | WO-2011023650 A1 | 3/2011 |
| WO | WO 2011/057240 | 5/2011 |
| WO | WO-2011058311 A1 | 5/2011 |
| WO | WO-2011063818 A1 | 6/2011 |
| WO | WO-2011113728 A1 | 9/2011 |
| WO | WO-2011128651 A1 | 10/2011 |
| WO | WO-2011152368 A1 | 12/2011 |
| WO | WO-2012009370 A2 | 1/2012 |
| WO | WO-2012035787 A1 | 3/2012 |
| WO | WO-2012074512 A1 | 6/2012 |
| WO | WO-2012146656 A1 | 11/2012 |
| WO | WO-2012150235 A1 | 11/2012 |
| WO | WO-2012168298 A1 | 12/2012 |
| WO | WO-2013014317 A1 | 1/2013 |
| WO | WO-2013029652 A1 | 3/2013 |
| WO | WO-2013060732 A1 | 5/2013 |
| WO | WO-2013175306 A2 | 11/2013 |
| WO | WO-2014003957 A1 | 1/2014 |
| WO | WO 2017/174332 | 10/2017 |
| WO | WO 2018/077872 | 5/2018 |
| WO | WO-2019020550 A2 | 1/2019 |
| ZA | 9605526 B | 2/1997 |

OTHER PUBLICATIONS

International Preliminary Report on Patentability for Application No. PCT/EP2017/077154, dated May 9, 2019, 8 pages.

International Preliminary Report on Patentability for Application No. PCT/GB2012/000587, dated Jan. 23, 2014, 12 pages.

International Search Report and Written Opinion for Application No. PCT/GB2012/000587, dated Oct. 8, 2013, 17 pages.

KCI Licensing Inc, "Prevena™ Incision Management System—Clinician Guide—Instructions for Use," 390061 Rev D, Jan. 2010, 10 pages.

KCI Licensing Inc, "Prevena™ Incision Management System—Clinician Guide—Instructions for Use," 390153-WEB Rev B, Jan. 2010, 12 pages.

KCI Licensing, "Prevena™ Incision Management System—Patient Guide", 390064 Rev D, Jan. 2010, 4 pages.

KCI Licensing, "Prevena™ Incision Management System—Patient Guide," 390152-WEB C, Jan. 2011, 6 pages.

KCI Licensing, Prevena™ Incision Management System, Jun. 22, 2010, in 2 pages.

Notice of Opposition—Statement of Facts and Evidence for the European Patent No. 2731564, mailed Jan. 22, 2020, 12 pages.

Smith & Nephew, Allevyn Gentle Border Multisite, Jun. 2011, 2 pages.

Smith and Nephew Inc., "Allevyn Wound Dressings Pamphlet," 2008, 2 pages.

International Search Report and Written Opinion, re PCT Application No. PCT/EP2017/077154, dated Dec. 1, 2017.

\* cited by examiner

MULTI-LAYERED WOUND DRESSING AND METHOD OF MANUFACTURE

CROSS-REFERENCE TO RELATED APPLICATIONS

This application is a U.S. national stage application of International Patent Application No. PCT/EP2017/077154, filed on Oct. 24, 2017, which claims priority to GB Application No. 1618298.2, filed Oct. 28, 2016, entitled MULTI-LAYERED WOUND DRESSING AND METHOD OF MANUFACTURE.

BACKGROUND

Field

The present invention relates to a multi-layered wound dressing and a method of manufacturing such a wound dressing. In particular, but not exclusively, embodiments of the present invention relate to a multi-layered wound dressing having a fibrous absorbent layer that can resist shrinkage even under extreme sterilisation methods and storage conditions, have improved aesthetics and mechanical strength and thereby increase consistency of product over its shelf life.

Description of the Related Art

Wound dressings can be formed with a liquid-impermeable top layer (outer layer, furthest from the wound), which prevents wound exudates striking through and leaking from the dressing. The top layer is often also gas permeable and liquid vapour permeable, to help minimise maceration to the wound.

In some known wound dressings, the liquid-impermeable top layer can be susceptible to wrinkling (wrinkling includes but is not limited to inconsistent appearance, crinkles, creases textured surface). Wrinkling may occur whilst the wound dressing is packaged in a sterile packaging, and may be due to shrinking of one or more wound dressing layers over time. This may be due to the type of packaging and sterilisation method chosen. It could be perceived by a medical practitioner that if wrinkling is present the product has been compromised. Thus, it may not be possible to determine whether the wound dressing is still suitable for use. Wrinkling of the top layer may also occur whilst the wound dressing is in use. A wrinkled wound dressing is also visually unappealing to a patient.

Wound dressings often require a product shelf life of as long as possible, typically 5 years, so it is desirable to produce a wound dressing in which the liquid impermeable top layer is not as likely to wrinkle, become inconsistent in appearance or change aesthetics over time.

EP 1,314,410 discloses a multi-layered wound dressing having top film layer, but does not disclose any way of reducing or preventing shrinkage or wrinkling of the dressing.

SUMMARY

According to a first aspect of the present invention there is provided a multi-layered wound dressing comprising:
  a fibrous absorbent layer for absorbing exudate from a wound site; and
  a support layer configured to reduce shrinkage of at least a portion of the wound dressing.

According to a second aspect of the present invention there is provided a method of manufacturing a multi-layered wound dressing, the method comprising:
  forming a support layer;
  forming a fibrous absorbent layer for absorbing exudate from a wound site; and
  laminating the support layer and the absorbent layer together to form the wound dressing;
  wherein the support layer is configured to reduce shrinkage of at least a portion of the wound dressing.

According to a third aspect of the present invention there is provided a method of treating a wound comprising placing a multi-layered wound dressing according to any embodiment disclosed herein over a wound.

According to a fourth aspect of the present invention there is provided a method of providing negative pressure wound therapy to a wound, the method comprising:
  placing a multi-layered wound dressing according to any embodiment disclosed herein over a wound;
  forming a fluid flow path between the wound dressing and a negative pressure source; and
  operating the negative pressure source to provide negative pressure to the wound.

According to a fifth aspect of the present invention there is provided a method of operating a negative pressure wound system, the method comprising:
  operating a negative pressure source fluidically connected to a multi-layered wound dressing according to any embodiment disclosed herein, the wound dressing configured to be positioned over a wound.

According to a sixth aspect of the present invention there is provided a negative pressure wound therapy kit comprising a multi-layered wound dressing according to any embodiment disclosed herein and a negative pressure source configured to be fluidically connected to the wound dressing.

According to another aspect there is provided a multi-layered wound dressing comprising:
  a fibrous absorbent layer for absorbing exudate from a wound site; and
  a support layer configured to reduce shrinkage of at least a portion of the wound dressing,
wherein the support layer comprises a net, the net comprises a geometric structure having a plurality of substantially geometric apertures extending therethrough; and
the geometric structure comprises a plurality of bosses substantially evenly spaced and joined by polymer strands to form the substantially geometric apertures between the polymer strands.

According to another aspect there is provided a multi-layered wound dressing comprising:
  a fibrous absorbent layer for absorbing exudate from a wound site; and
  a support layer configured to reduce shrinkage of at least a portion of the wound dressing,
wherein the net is formed from high density polyethylene.

According to another aspect there is provided a multi-layered wound dressing comprising:
  a fibrous absorbent layer for absorbing exudate from a wound site; and
  a support layer configured to reduce shrinkage of at least a portion of the wound dressing,
wherein the support layer has a tensile strength from 0.05 to 0.06 Nm.

According to another aspect there is provided a multi-layered wound dressing comprising:

a fibrous absorbent layer for absorbing exudate from a wound site; and a support layer configured to reduce shrinkage of at least a portion of the wound dressing, wherein the support layer is bonded to fibres in a top surface of the absorbent layer, the support layer further comprises a bonding layer, wherein the support layer is heat laminated to the fibres in the absorbent layer via the bonding layer; and wherein the bonding layer comprises a low melting point ethylene-vinyl acetate adhesive.

Certain embodiments of the invention provide the advantage that at least part of the wound dressing is less likely to shrink over time compared to known wound dressings.

Certain aspects of the invention provide a wound dressing in which wrinkling in a layer or layers of a wound dressing, e.g. a liquid impermeable film layer is prevented or reduced.

BRIEF DESCRIPTION OF THE DRAWINGS

Embodiments of the invention are further described hereinafter with reference to the accompanying drawings, in which.

In the drawings like reference numerals refer to like parts.

Figure 1:
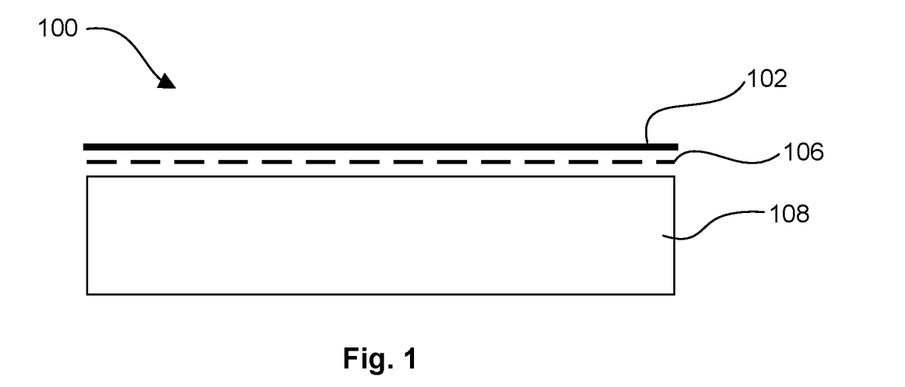
FIG. 1 is a schematic diagram of a section of an example of a wound dressing.

FIG. 1 shows an example of a multi-layer wound dressing 100. The wound dressing 100 includes a liquid impermeable film layer 102 located at the top of the wound dressing 100. In use, the film layer 102 is the top layer of the wound dressing 100, most distal from a wound site.

The film layer 102 is also gas and vapour permeable to allow for evaporation of fluid or wound exudate from the wound dressing 100, and help prevent maceration of the wound. In this example, the film layer 102 is formed from a polyurethane blend, though other suitable materials may include other polymeric materials, for example polyethylene, or polypropylene.

An absorbent layer 108 underlies the film layer 102. The absorbent layer 108 has a fibrous structure for absorbing exudate from a wound site. In this example, the absorbent layer 108 includes superabsorbent fibres. The absorbent layer 108 also includes other fibres. In this example, the absorbent layer includes superabsorbent fibres, viscose fibres and polyester fibres.

In this example, the absorbent layer 108 includes around 40% superabsorbent fibres, 40% viscose fibres, and 20% polyester fibres. In other examples, the absorbent layer may include around 0-50% superabsorbent fibres, 0-100% viscose fibres and 0-50% polyester fibres. Suitable superabsorbent fibres include crosslinked acrylate copolymer fibres that are partially neutralized to sodium salt however other superabsorbent fibres are available. The absorbent layer 108 may be manufactured using a needling process in which the fibres are mechanically tangled together.

In other examples, the absorbent layer may include other ratios of superabsorbent, viscose and polyester fibres. For example, the absorbent layer may include around 50% superabsorbent fibres, 35% viscose fibres and 20% polyester fibres. Alternatively, the absorbent layer may include 40% superabsorbent fibres and 60% viscose fibres.

The film layer 102 is located over the absorbent layer 108 so that wound exudate collected in the absorbent layer 108 can evaporate out of the wound dressing 100 through the film layer 102.

A support layer 106 is located between the film layer 102 and the absorbent layer 108. The support layer 106 helps to reinforce the structure of the absorbent layer 108 and thereby reduce shrinkage of the wound dressing 100. The support layer 102 also helps to provide extra mechanical strength to the film layer 102 to reduce or prevent wrinkling of the film layer 102 over time. The mechanical strength also reduces the chance of the dressing deforming or rolling up causing a pressure point.

Aptly, the support layer 106 is configured to have a tensile strength from 0.05 to 0.06 Nm to provide mechanical strength to the surrounding layers (e.g. the film layer 102 and the absorbent layer 108) without compromising the flexibility of the wound dressing 100. The support layer 106 may have a thickness of from 50 to 150 µm. Aptly, the support layer 106 may have a thickness of around 100 to 110 µm.

Figure 2:
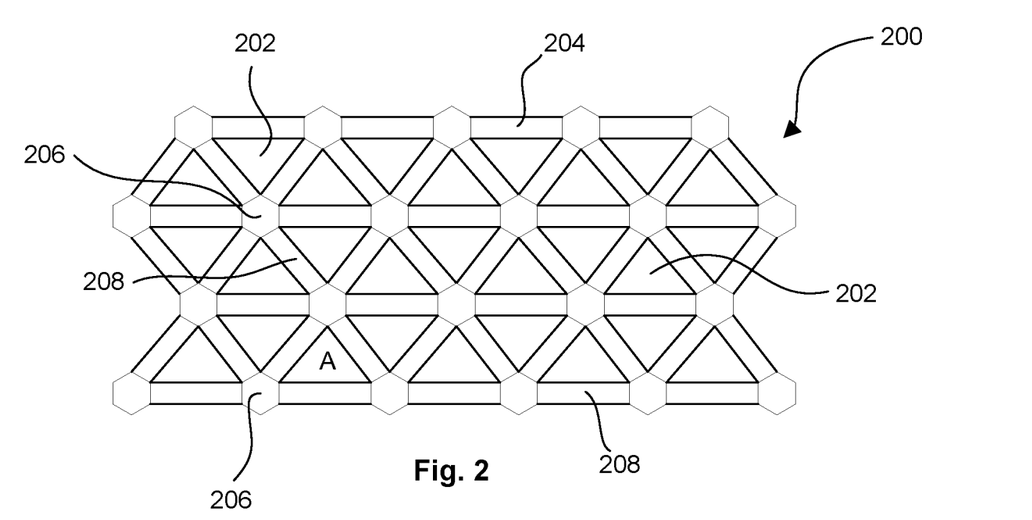
FIG. 2 is a schematic diagram of an example of a support layer.

Referring to FIG. 2, the support layer 106 includes a net 200 configured to reduce shrinkage of the wound dressing 100. Aptly, the net 200 is configured to reduce shrinkage of the absorbent layer 108 and/or the film layer 102 to help reduce wrinkling of the film layer 102.

In this example, the net 200 has a substantially hexagonal (or honeycomb) structure 204 including a plurality of substantially triangular shaped apertures 202 extending therethrough.

The hexagonal structure 204 is formed from a plurality of dots (or bosses) 206 joined by polymer strands 208. The dots 206 are substantially evenly spaced with respect to each other. Each dot forms a vertex of the hexagonal pattern in the structure 204. Each dot 206 is joined to six surrounding dots 206 by polymer strands 208. That is, six polymer strands 208 extend from each dot 206 and each connect to a respective surrounding dot 206 to form the hexagonal structure 204 having triangular shaped apertures 202 between the polymer strands 208.

Each of the triangular shaped apertures 202 may have an area A of from 0.005 to 0.32 mm$^2$. This allows liquid vapour from a wound to pass freely through the apertures, whilst still providing sufficient strength to the support layer 106.

It can also be said that the structure 204 is a structure comprising a plurality of strands or struts that are joined to form a plurality of triangles. In this example the triangles tessellate in rows. It will be appreciated that the strands or struts may be arranged in other formations, for example squares, diamonds or rectangles with different geometries and therefore differing open areas.

In this example, the support layer 106 is located directly adjacent the absorbent layer 108. As such, the support layer 106 can effectively provide additional mechanical strength to fibres in the top surface of the absorbent layer 108. This can help prevent movement of the fibres and reduce shrinking of the absorbent layer 108.

Aptly, the support layer 106 is bonded to the fibres in the top surface of the absorbent layer 108. This can help to lock the fibres in position and prevent or reduce any movement.

In this example, the support layer 106 further includes a bonding layer for heat laminating the net 200 to the absorbent layer 108. The support layer 106 is thus heat laminated to fibres in the absorbent layer 108 via the bonding layer.

The bonding layer contained within the net has a lower melting temperature than the net 200 so that the support layer 106 can be heat laminated to the absorbent layer 108 whilst maintaining the structure of the net 200. The bonding layer can be formed from a low melting point polymer, for example a low melting point ethylene-vinyl acetate, whilst the net 200 may be formed from a high density polyethylene, which melts at a higher temperature than the bonding layer. Other polymers having a lower melting point than the net 200 may also be suitable. For example the bonding layer may be a separate layer or alternatively include an ethylene-acrylate or thermoplastic polyurethane based adhesive.

The net 200 and the bonding layer can be coextruded to form the support layer 106. Aptly, the bonding layer is extruded with a similar structural shape to the net 200, so that the apertures 202 in the net 200 are not obstructed by the bonding layer. This helps to ensure that exudate the absorbent layer 108 can pass through the support layer and evaporate out of the wound dressing 100 through the film layer 102.

Figure 3A:
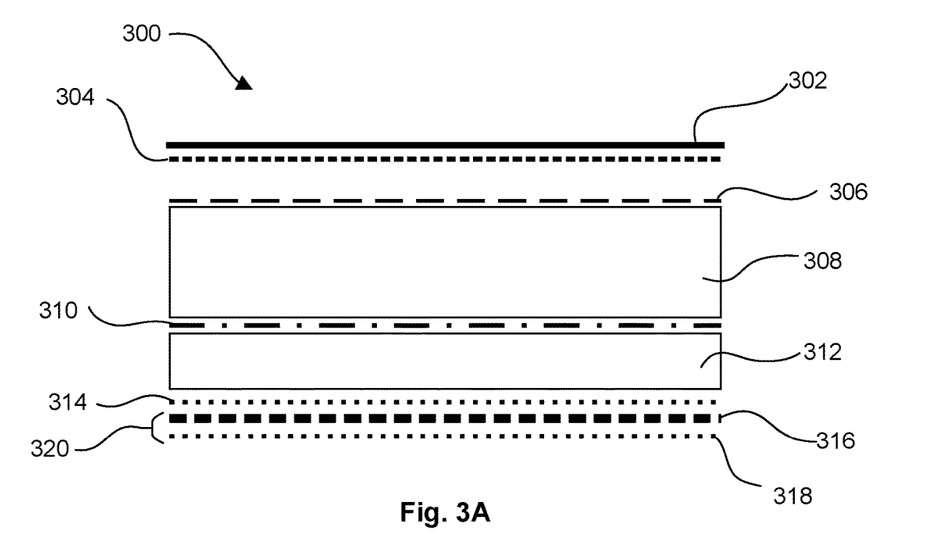
FIG. 3A is a schematic diagram of a section of another example of a wound dressing.
Figure 3B:
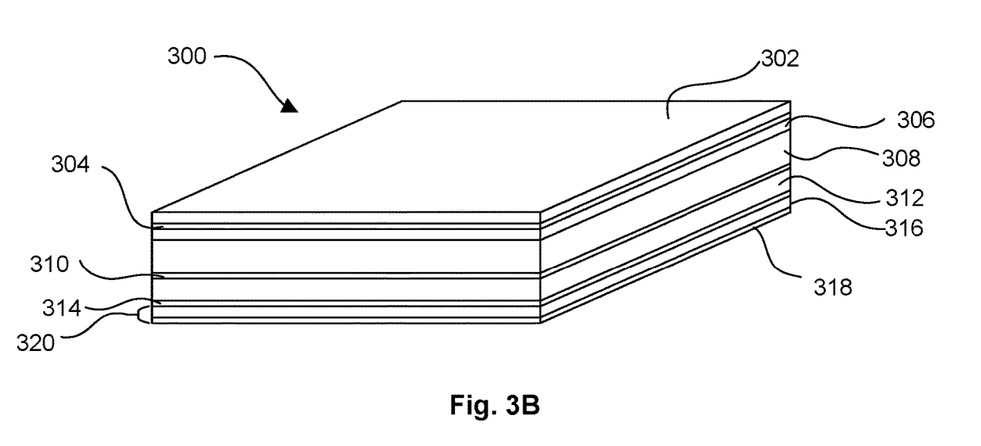
FIG. 3B is a perspective view of the wound dressing of FIG. 3A.

FIG. 3 illustrates another example of a multi-layered wound dressing 300. The wound dressing 300 includes a film layer 302, support layer 306 and absorbent layer 308, the same as the film layer 102, support layer 106 and absorbent layer 108 described in relation to FIG. 1.

The wound dressing 300 also includes a first adhesive layer 304, located between the film layer 302 and the support layer 306, for attaching the film layer 302 to the support layer 306. The first adhesive layer 304 is a hot melt adhesive applied to a wound facing side (underside) of the film layer 302. Aptly, the first adhesive layer 304 is pattern coated onto the film layer 302, to include holes, so that gas and liquid vapour can pass through holes in the first adhesive layer 304. In other examples the film layer 302 may be laminated (e.g. heat laminated) directly onto the support layer 306 without the need for an adhesive layer 304 in between.

In this example, the wound dressing 300 also includes a foam layer 312, which is a fluid transport layer. The foam layer 312 is located under the absorbent layer 306. The foam layer 312 acts to draw fluid away from a wound site and transport the fluid to the absorbent layer 308. The foam layer may be formed from an open cell polyurethane foam and other options are available, as will be recognised by those skilled in the art.

An adhesive web layer 310 is located between the foam layer 312 and the absorbent layer 308 to adhere the foam layer 312 to the absorbent layer 308. The adhesive web layer may be formed from bicomponent polypropylene/polyethylene fibres. Such bicomponent fibres are known in the art, so for brevity will not be discussed in detail. The adhesive web layer 310 includes a plurality of apertures extending therethrough to allow for passage of exudate from the foam layer 312 to the absorbent layer 108.

The wound dressing 300 also includes a wound contact layer 320, which includes a perforated film 316. The perforated film 316 is located under the foam layer 312 and helps to prevent the wound dressing 300 from attaching to the wound as the wound heals. For example, where the wound dressing 300 includes the foam layer 312, the perforated film 316 can prevent new tissue from growing into cells of the foam layer 312. In other examples, the foam layer 312 may not be present and the perforated film 316 can help prevent fibres of the absorbent layer 308 from becoming embedded in the wound. Perforations in the perforated film 316 are aptly substantially uniformly distributed and are of suitable size to allow passage of exudate into the wound dressing 300, e.g. with holes having a diameter of 1-2.5 mm. The perforated film 316 is aptly formed from polyurethane.

The wound contact layer 320 may also include an adhesive 318 located under the perforated film 316 (i.e. on the wound facing side of the perforated film 316) for adhering the wound dressing 300 to the skin. In this case the adhesive is silicone 318 and is aptly spread onto the underside of the perforated film with a coat weight of around 30-200 g/m$^2$. In some other examples, an additional attachment element, for example bandages, strips of tape, or compression bandages may be used to secure the wound dressing 300 to the patient.

The top side of the perforated film 316 (i.e. the side distal from the wound) may be coated with a further adhesive layer 314. The further adhesive layer 314 adheres the wound contact layer 320 to the foam layer 312. Aptly, the further adhesive layer 314 may be an acrylic adhesive, though other suitable adhesives may also be used. In other examples the wound contact layer 320 may be laminated (e.g. heat laminated) directly to the foam layer 312, without the need for the further adhesive layer 314 in between.

Figure 4:
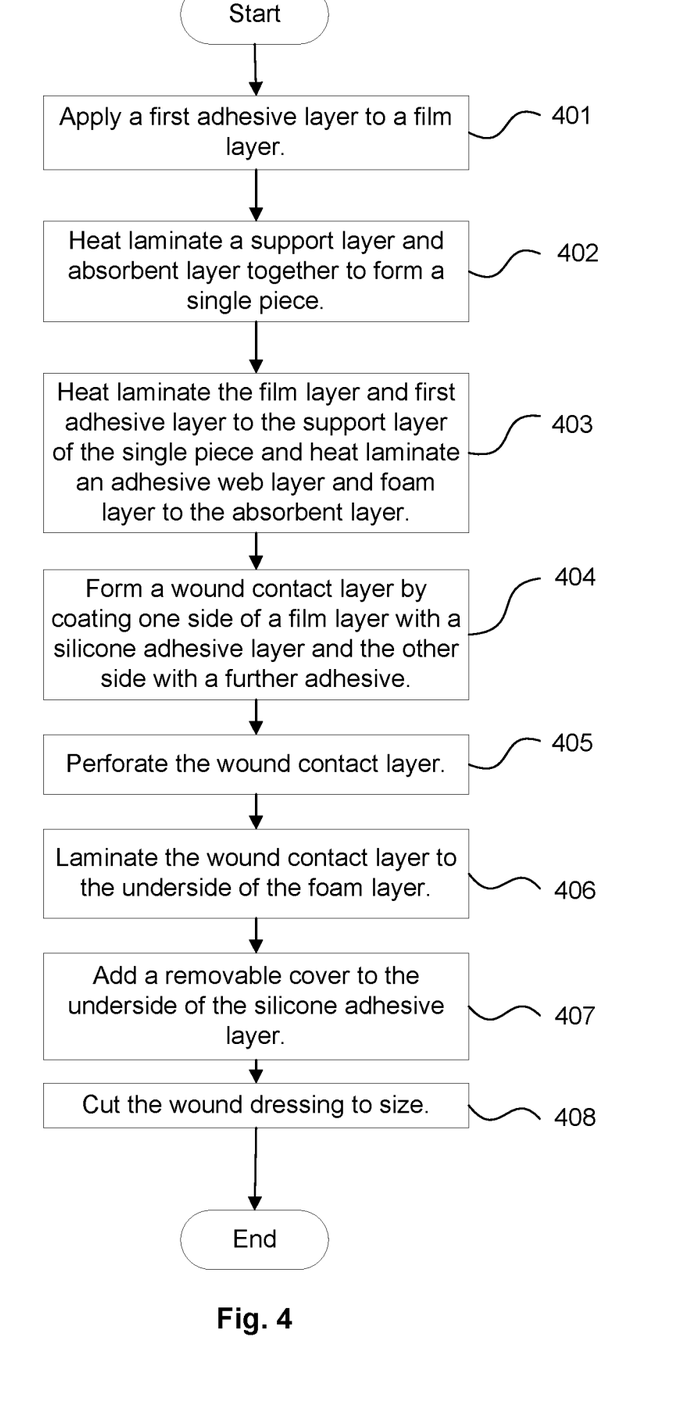
FIG. 4 is a flow diagram of an example of a method of manufacturing the wound dressing of FIG. 3A.

FIG. 4 illustrates an example of a method of manufacturing the wound dressing 300. The method is not limited to the steps shown and, as described above, may include additional steps. The method also is not limited to the order shown in FIG. 4. As will be appreciated by those skilled in the art, several of the method steps shown may be performed in a different order. In some embodiments, the wound dressing 300 is manufactured by forming each of the layers, and assembling the layers in the correct order, before heat laminating them together.

The film layer 302 may be formed by extrusion. At step 401, the first adhesive layer 304 is applied to the film layer. Aptly, the first adhesive layer 304 is pattern coated onto the underside of the extruded film layer 302.

At step 402 the support layer 306 and the absorbent layer 308 are heat laminated together to form a single piece. At step 403 the film layer 302 and first adhesive layer 304 are heat laminated to the support layer 306 on the top side of the single piece and the adhesive web layer 310 and foam layer 312 are heat laminated to the absorbent layer 308. Whilst the layers have been described as being heat laminated together in a specific order, the layers may be separately laminated together or laminated together all at the same time.

At step 404 the wound contact layer 320 is formed by coating one side of a film layer with the silicone adhesive layer 314, and coating the other side of the film layer with a further adhesive layer 314. The film layer is then perforated at step 405 (e.g. by needle punching), to form the wound contact layer 320 including the perforated film 316, the silicone adhesive layer 314 for contacting the wound and the further adhesive layer 314. Alternatively, the film layer may be perforated before adding the further adhesive layer 314.

The wound contact layer may then be laminated (e.g. with heat, ultrasonic and/or radio frequency welding) to the underside of the foam layer 312 to form the wound dressing 300, as shown at step 406.

At step 407 a removable cover may be applied to the underside of the silicone adhesive layer 318. This cover can be removed before the wound dressing 300 is applied to a patient.

At step 408 the wound dressing 300 may be cut into separate wound dressing pieces, each suitably sized for an intended application.

Figure 5:
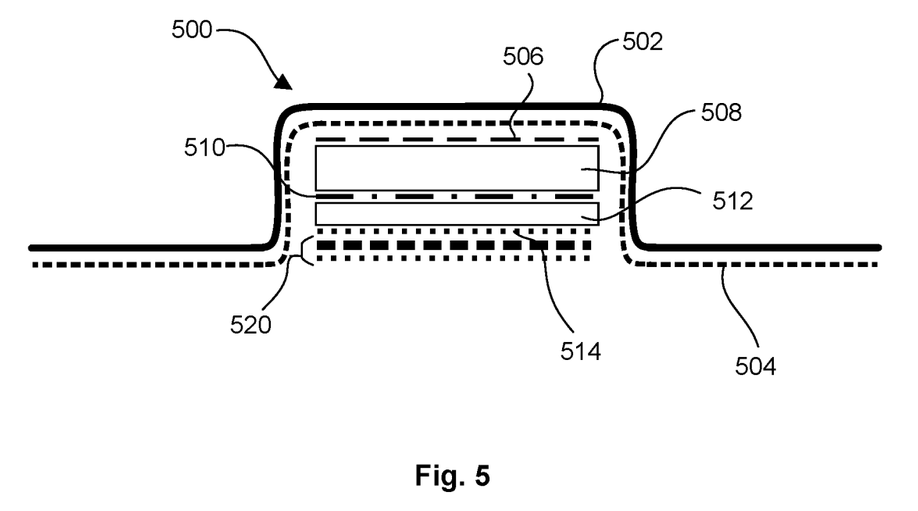
FIG. 5 is a schematic diagram of a further example of a wound dressing.

In another example, as shown in FIG. 5, the film layer 502 may have a larger surface area than the remainder of the wound dressing 500 so that it extends further outwardly than the other layers of the wound dressing. The wound-facing (underside) of the film layer may be coated with a pressure sensitive adhesive 504 (or other suitable adhesive) for sticking the dressing to the patient around the wound periphery. The pressure sensitive adhesive 504 may also adhere the film layer 502 to the support layer 506 of the wound dressing 500. The wound dressing may also include an absorbent layer 508, adhesive web layer 510, foam layer 512, further adhesive layer 514 and wound contact layer 520. Each of the layers in this example may be similar to corresponding layers described above in relation to FIGS. 3A and 3B, so for brevity will not be described again in detail.

In this example, the wound dressing may be manufactured following steps 401 to 407 described above. However, instead of cutting the dressing to size (step 408) each wound dressing may be made individually with each layer cut or formed to the desired size prior to laminating all the layers together so that the final wound dressing has a film layer larger than the other layers.

Figure 6:
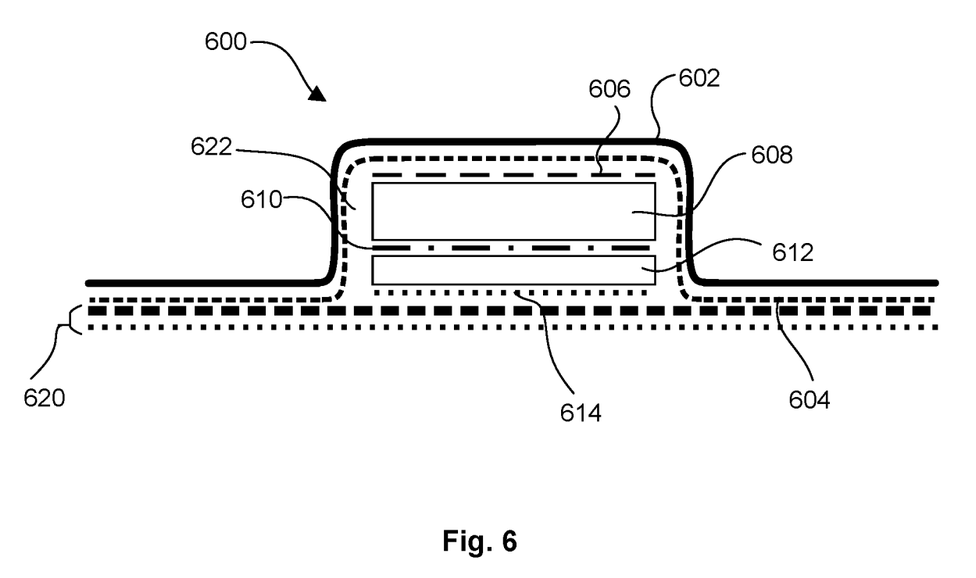
FIG. 6 is a schematic diagram of a yet further example of a wound dressing.

In a further example, as shown in FIG. 6, both the wound contact layer 620 and the film layer 602 may extend beyond the remaining layers of the wound dressing 600. The wound contact layer 620 and the film layer may be adhered together around the periphery (e.g. via an adhesive layer 604), so that the remaining layers of the wound dressing are sandwiched between the wound contact layer 620 and the film layer 602. In other words the support layer 606, the absorbent layer 608, the adhesive web layer 610, and the foam layer 612 may be sealed within a cavity 622 between the film layer 602 and the wound contact layer 620. In this example, a further adhesive layer 614 adheres the foam layer 612 to the wound contact layer 620, though in other examples the further adhesive layer 614 may not be required. Each of the layers in this example may be similar to corresponding layers described above in relation to FIGS. 3A and 3B, so for brevity will not be described again in detail.

The wound dressing 600 in this example may be manufactured similarly to the wound dressing 300, as described above, but with the film layer 602 and the wound contact layer 620 being laminated together around the periphery (e.g. via the adhesive layer 604) to sandwich the remaining layers between the film layer 602 and the wound contact layer 620. Alternatively, the film layer 602 may be directly laminated around the periphery (e.g. heat laminated) to the wound contact layer 620, without the need for the additional adhesive layer 604.

Although the wound dressings 300, 500, 600 have been described having several adhesive layers, one or more of these layers may not be present. For example, the perforated film itself may be formed from a hot melt adhesive material so that it can be directly heat laminated onto the foam layer, in which case the further adhesive layer may not be needed. In another example, the adhesive web layer may not be present if the foam and absorbent layers are adhered in another way. For example, the foam and absorbent layers may be directly chemically bonded together. Similarly, the first adhesive layer may not be needed. For example if the support layer includes an adhesive material, or if the film layer itself is formed from a hot melt adhesive then the film layer and the support layer may be directly adhered together.

In another example, the wound dressing may be provided without the foam layer. The foam layer helps to transport exudate away from the wound. However in some cases, and depending on the severity of a wound, the absorbent layer may sufficiently draw exudate from the wound without the need for the foam layer.

Although in the examples described above, the support layer is heat laminated to the absorbent layer via a bonding layer, other laminating techniques may be suitable. For example, the bonding layer may include a pressure sensitive adhesive. In this case, heat may not be required to laminate the support layer and adhesive layer together.

Although in the example described above, the net layer has been described as having a substantially hexagonal shaped structure, other geometric structures may also be suitable.

With other geometric structures, the apertures may also have different geometric shapes.

In another example, the wound dressing may include more than one support layer to provide support to other layers in the wound dressing. For example a first support layer may be located between the liquid impermeable film layer and the absorbent layer, and a further support layer may be located between the absorbent layer and the fluid transport layer (foam layer). This may help to support the absorbent layer from both sides to further reduce shrinking of the absorbent layer.

Any of the examples described herein may be adapted for use with a negative pressure system (sometimes referred to as a reduced pressure system) including a source of negative pressure, such as a negative pressure pump. For example, the film layer may include a negative pressure interface, such as a port, to which a negative pressure supply tube may be connected. The supply tube may be connected to a negative pressure source so that, in use, the negative pressure source applies a negative pressure to the wound dressing between the film layer and the wound to help draw wound exudate away from the wound and into the absorbent layer of the dressing.

Figure 7:
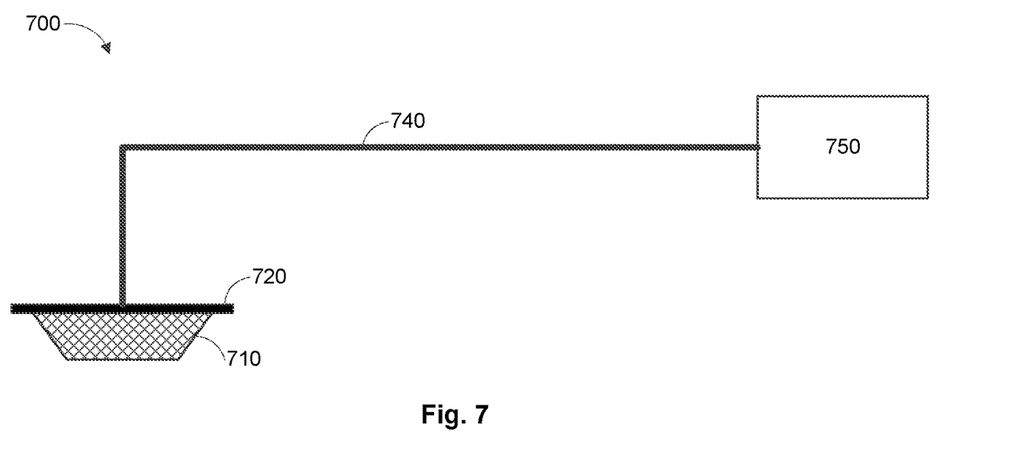
FIG. 7 is a schematic diagram of an example of a negative pressure wound therapy system.

FIG. 7 illustrates an example of a negative pressure wound therapy system 700. The system includes a wound cavity 710 covered by a wound dressing 720, which can be a dressing according to any of the examples described herein. The dressing 720 can be positioned inside the wound cavity 710 and further seal the wound cavity so that negative pressure can be maintained in the wound cavity. For example, a film layer of the wound dressing 720 can provide substantially fluid impermeable seal over the wound cavity 710. A single or multi lumen tube or conduit 740 connects the wound dressing 720 with a negative pressure device 750 configured to supply reduced pressure. The negative pressure device 750 includes a negative pressure source. The negative pressure device 750 can be a canisterless device (meaning that exudate is collected in the wound dressing and/or is transferred via the tube 740 for collection to another location). In some embodiments, the negative pressure device 750 can be configured to include or support a canister. Additionally, in any of the embodiments disclosed herein, the negative pressure device 750 can be fully or partially embedded in, mounted to, or supported by the wound dressing 720.

The conduit 740 can be any suitable article configured to provide at least a substantially sealed fluid flow path or pathway between the negative pressure device 750 and the wound cavity 710 so as to supply reduced pressure to the wound cavity. The conduit 740 can be formed from polyurethane, PVC, nylon, polyethylene, silicone, or any other suitable rigid or flexible material. In some embodiments, the wound dressing 720 can have a port configured to receive an end of the conduit 740. For example, a port can include a hole in the film layer. In some embodiments, the conduit 740 can otherwise pass through and/or under a film layer of the wound dressing 720 to supply reduced pressure to the wound cavity 710 so as to maintain a desired level of reduced pressure in the wound cavity. In some embodiments, at least a part of the conduit 740 is integral with or attached to the wound dressing 720.

In use, the wound dressing, such as the wound dressing 100, 300, 500, or 600, is applied to a wound site with the wound contact layer 320 contacting the wound. Exudate from the wound may pass through the perforated film 116 and into the foam layer 312, which acts to transport wound exudate away from the wound into the absorbent layer 308. Wound exudate collected in the absorbent layer 308 can evaporate from the wound dressing 300 through the vapour permeable film layer 302.

The support layer helps to provide mechanical strength to the absorbent layer, which may swell when it is wet and may shrink as it dries. The support layer can help to minimise movement of fibres in the absorbent layer at least on the side distal from the wound and thus helps to prevent shrinking of the wound dressing, particularly in this region. Minimising shrinking of the wound dressing in this way can in turn can help to prevent wrinkling of the film layer. It also reduced the chance of the dressing rolling/folding up under secondary retention.

As the wound dressing becomes exposed to moisture (either from the wound or the surrounding atmosphere), it may swell or expand causing increased wrinkling of the film layer. Having the support layer adhered to the film layer can help to provide support to the film layer and resist wrinkling of the film layer by providing additional mechanical strength to the film layer.

The above described wound dressings are less likely to exhibit shrinking whilst stored in sterile packaging than previously known wound dressings. Thus, wrinkling of the film layer on the outside of the wound dressing can be prevented or reduced. A medical practitioner is therefore less likely to disregard a wound dressing that is still within its recommended shelf life, sterile and suitable for use, purely because of visual appearance of the film layer.

The hexagonal and/or triangular shape of the net structure of the support layer helps to provide mechanical strength and can be particularly effective at resisting against shrinkage of surrounding wound dressing layers.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A multi-layered wound dressing comprising:
a fibrous absorbent layer for absorbing exudate from a wound site;
a support layer configured to reduce shrinkage of at least a portion of the multi-layered wound dressing; and
a liquid impermeable film layer,
wherein the support layer is located between the absorbent layer and the film layer, and
wherein the support layer has a tensile strength from 0.05 to 0.06 Nm.

2. A multi-layered wound dressing according to claim 1, wherein the support layer comprises a net.

3. A multi-layered wound dressing according to claim 2, wherein the net comprises a geometric structure having a plurality of substantially geometric apertures extending therethrough.

4. A multi-layered wound dressing according to claim 3, wherein the geometric structure comprises a plurality of bosses substantially evenly spaced and joined by polymer strands to form the plurality of substantially geometric apertures between the polymer strands.

5. A multi-layered wound dressing according to claim 4, wherein the geometric structure of the net comprises a hexagonal structure, and wherein the plurality of substantially geometric apertures have triangular shape.

6. A multi-layered wound dressing according to claim 5, wherein a boss of the plurality of bosses form a vertex of the hexagonal structure with polymer strands extending from the boss and connecting the boss to neighboring bosses, and wherein the plurality of substantially geometric apertures are formed between neighboring polymer strands.

7. A multi-layered wound dressing according to claim 2, wherein the net is formed from high density polyethylene.

8. A multi-layered wound dressing according to claim 3, wherein the plurality of substantially geometric apertures have an area from 0.005 to 0.32 mm$^2$.

9. A multi-layered wound dressing according to claim 1, wherein the support layer has a thickness of from 50 to 150 µm.

10. A multi-layered wound dressing according to claim 1, wherein the support layer is located directly adjacent the absorbent layer.

11. A multi-layered wound dressing according to claim 1, wherein the support layer is bonded to fibres in a top surface of the absorbent layer.

12. A multi-layered wound dressing according to claim 11, wherein the support layer further comprises a bonding layer, wherein the support layer is heat laminated to the fibres in the absorbent layer via the bonding layer.

13. A multi-layered wound dressing according to claim 12, wherein the bonding layer comprises a low melting point ethylene-vinyl acetate adhesive, and wherein the support layer comprises a net formed from a material with a higher melting temperature than that of the bonding layer.

14. A multi-layered wound dressing according to claim 1, further comprising an adhesive layer attaching the film layer to the support layer.

15. A multi-layered wound dressing according to claim 1, further comprising a wound contact layer located adjacent the absorbent layer for positioning adjacent a wound.

16. A multi-layered wound dressing according claim 15, further comprising a fluid transport layer between the wound contact layer and the absorbent layer for transporting exudate away from a wound into the absorbent layer.

17. A method of treating a wound comprising placing a multi-layered wound dressing according to claim 1 over a wound.

18. A method of manufacturing a multi-layered wound dressing, the method comprising:
   forming a support layer that comprises a net layer and a bonding layer by coextruding the net layer and the bonding layer;
   forming a fibrous absorbent layer for absorbing exudate from a wound site; and
   laminating the support layer and the absorbent layer together to form the wound dressing by attaching the bonding layer to the absorbent layer;
   wherein the support layer is configured to reduce shrinkage of at least a portion of the multi-layered wound dressing, and
   wherein the support layer has a tensile strength from 0.05 to 0.06 Nm.

19. A method according to claim 18, wherein the bonding layer is formed from a polymer with a first melting temperature and the net layer is formed from a material with a second melting temperature higher than the first melting temperature of the polymer of the bonding layer, and wherein laminating the support layer and the absorbent layer comprises laminating by using heat so that the net layer maintains its structure during application of heat.

20. A method according to claim 18, further comprising heat laminating the support layer to fibres in the absorbent layer via the bonding layer, wherein the bonding layer comprises a low melting point ethylene-vinyl acetate adhesive, and wherein the support layer comprises a net formed from a material with a higher melting temperature than that of the bonding layer.

* * * * *

UNITED STATES PATENT AND TRADEMARK OFFICE
CERTIFICATE OF CORRECTION

PATENT NO. : 11,559,437 B2
APPLICATION NO. : 16/345196
DATED : January 24, 2023
INVENTOR(S) : Daniel Lee Steward It is certified that error appears in the above-identified patent and that said Letters Patent is hereby corrected as shown below:

In the Specification

Column 3, Line 41, below "In the drawings like reference numerals refer to like parts." insert -- DETAILED DESCRIPTION --, as a new heading.

Column 8, Line 14-15, delete "With other geometric structures, the apertures may also have different geometric shapes." and insert the same on Column 8, Line 13 as a continuation of the same paragraph.

In the Claims

Column 11, Line 7, in Claim 16, after "according" insert -- to --.

Signed and Sealed this
Fourth Day of April, 2023

Katherine Kelly Vidal
*Director of the United States Patent and Trademark Office*